(12) United States Patent
Rii et al.

(10) Patent No.: US 12,377,116 B2
(45) Date of Patent: Aug. 5, 2025

(54) COMPOSITION FOR ENHANCING EFFECT OF ANTIBODY DRUG

(71) Applicants: AUREO CO., LTD., Kimitsu (JP); NATIONAL CENTER FOR CHILD HEALTH AND DEVELOPMENT, Tokyo (JP)

(72) Inventors: Ko Rii, Tokyo (JP); Masayuki Fujino, Tokyo (JP); Yukiko Moriya, Kimitsu (JP)

(73) Assignees: AUREO CO., LTD., Kimitsu (JP); NATIONAL CENTER HEALTH AND DEVELOPMENT, Tokyo (JP)

( * ) Notice: Subject to any disclaimer, the term of this patent is extended or adjusted under 35 U.S.C. 154(b) by 724 days.

(21) Appl. No.: 17/631,704

(22) PCT Filed: Sep. 10, 2020

(86) PCT No.: PCT/JP2020/034361
§ 371 (c)(1),
(2) Date: Jan. 31, 2022

(87) PCT Pub. No.: WO2021/049587
PCT Pub. Date: Mar. 18, 2021

(65) Prior Publication Data
US 2022/0265698 A1    Aug. 25, 2022

(30) Foreign Application Priority Data
Sep. 11, 2019   (JP) .................. 2019-165722

(51) Int. Cl.
*A61K 31/716* (2006.01)
*A61P 35/00* (2006.01)
*C07K 16/28* (2006.01)

(52) U.S. Cl.
CPC ............ *A61K 31/716* (2013.01); *A61P 35/00* (2018.01); *C07K 16/2827* (2013.01)

(58) Field of Classification Search
CPC ........ A61K 31/716; A61K 9/0053; A61P 3/04
See application file for complete search history.

(56) References Cited

U.S. PATENT DOCUMENTS

| | | | |
|---|---|---|---|
| 8,802,433 B2 | 8/2014 | Moriya et al. | |
| 10,111,901 B2 | 10/2018 | Bose et al. | |
| 2008/0293669 A1 | 11/2008 | Moriya et al. | |
| 2010/0068184 A1 | 3/2010 | Moriya et al. | |
| 2012/0202771 A1 | 8/2012 | Moriya et al. | |
| 2015/0297651 A1 | 10/2015 | Moriya et al. | |
| 2017/0100424 A1* | 4/2017 | Bose | A61K 31/716 |

FOREIGN PATENT DOCUMENTS

| | | |
|---|---|---|
| JP | 2002-204687 A | 7/2002 |
| JP | 4000078 B2 | 10/2007 |
| JP | 4054697 B2 | 2/2008 |
| JP | 4369258 B2 | 11/2009 |
| JP | 5242855 B2 | 7/2013 |
| JP | 5331482 B2 | 10/2013 |
| JP | 5554221 B2 | 7/2014 |
| JP | 5559173 B2 | 7/2014 |
| JP | 5560472 B2 | 7/2014 |
| JP | 5715659 B2 | 5/2015 |
| JP | 5937029 B2 | 6/2016 |
| JP | 2017-524737 A | 8/2017 |
| JP | 6293187 B2 | 3/2018 |
| JP | 6380968 B2 | 8/2018 |
| WO | 2006/027914 A1 | 3/2006 |
| WO | 2016/007876 A1 | 1/2016 |
| WO | 2016/073763 A2 | 5/2016 |
| WO | 2017/120604 A1 | 7/2017 |

OTHER PUBLICATIONS

Liu et al., Combined yeast-derived β-glucan with anti-tumor monoclonal antibody for cancer immunotherapy, 2009, Experimental and Molecular Pathology, 86, 208-214. (Year: 2009).*

Extended European Search Report issued Sep. 19, 2023 in European Application No. 20862447.8.

Office Action dated Sep. 22, 2023 issued in corresponding CN patent application No. 202080061449.2.

English Translation of International Preliminary Report on Patentability dated Mar. 17, 2022 in International Application No. PCT/JP2020/034361.

Yasumasa Ishida, et al., "Induced expression of PD-1, a novel member of the immunoglobulin gene superfamily, upon programmed cell death", The EMBO Journal, 1992, pp. 3887-3895, vol. 11, No. 11.

Gordon J. Freeman, et al., "Engagement of the PD-1 Immunoinhibitory Receptor by a Novel B7 Family Member Leads to Negative Regulation of Lymphocyte Activation", J. Exp. Med., Oct. 2, 2000, vol. 192, No. 7.

Spencer C. Wei, et al., "Fundamental Mechanisms of Immune Checkpoint Blockade Therapy", Cancer Discovery, Sep. 2018, pp. 1069-1086.

Curtis A. Clark, et al., "Tumor-Intrinsic PD-L1 Signals Regulate Cell Growth, Pathogenesis, and Autophagy in Ovarian Cancer and Melanoma", Cancer Research, Dec. 1, 2016, pp. 6964-6974, vol. 76, No. 23.

Yoshiyuki Kimura, et al., "Antitumor and antimetastatic effects of β-glucan in clolon 26-implanted mice" Proceedings of the Japanese Cancer Association, 2004, p. 456, vol. 63, P-1197.

(Continued)

*Primary Examiner* — Scarlett Y Goon
*Assistant Examiner* — Samantha Lynn Schachermeyer
(74) *Attorney, Agent, or Firm* — Sughrue Mion, PLLC (57) ABSTRACT

Provided is a composition capable of enhancing the effect of an antibody drug such as an immune checkpoint inhibitor, etc. A β-glucan is used as an active ingredient of a composition for enhancing the effect of an antibody drug. This composition is used suitably for antibody drugs that have an effect of suppressing growth of cancer via immune checkpoint inhibition; e.g., antibody drugs including a monoclonal antibody to PD-L1.

1 Claim, 8 Drawing Sheets

(56) References Cited

OTHER PUBLICATIONS

Kaori Yamasaki, et al., "Antitumor effect by oral administration of extracellular β-glucan of black yeast", Lecture abstracts of the Annual Meeting of the Japan Society of Bioscience, Biotechnology, and Agrochemistry, Mar. 5, 2004, p. 165, vol. 3A07p24.
International Search Report for PCT/JP2020/034361 dated Oct. 27, 2020 [PCT/ISA/210].
Written Opinion for PCT/JP2020/034361 dated Oct. 27, 2020 [PCT/ISA/237].
International Preliminary Report on Patentability for PCT/JP2020/034361 dated Oct. 19, 2020 [PCT/IPEA/409].

* cited by examiner

Control group A (n=4):

Test group 1A (n=2):

Test group 2A (n=3):

Test group 3A (n=3):

⇩ : Saline
⇩ : M-β-Glucan (100mg/kg)
⬇ : PD-L1mAb: 200μg/head

[FIG. 8]

COMPOSITION FOR ENHANCING EFFECT OF ANTIBODY DRUG

CROSS REFERENCE TO RELATED APPLICATIONS

This application is a National Stage of International Application No. PCT/JP2020/034361 filed Sep. 10, 2020, claiming priority based on Japanese Patent Application No. 2019-165722 filed Sep. 11, 2019.

TECHNICAL FIELD

The present invention relates to a composition for enhancing the effect of an antibody drug.

BACKGROUND ART

Molecular targeted drugs that target immune checkpoints are attracting attention as novel cancer treatment methods. Immune checkpoints are a braking mechanism to prevent runaway so that activated immune cells do not attack normal tissues or cells; cancer cells, on the contrary, utilize this mechanism to avoid the attack of immune cells. This is one of the functions cancer cells use for their own survival, and there are aspects that have yet to be possible to clarify. As research in this field has progressed, it has been clarified in recent years that effective anti-cancer effects are obtained even in clinical practice by antibody drugs, etc., that inhibit the function of PD-1 and CTLA4, which are immune checkpoint molecules (see Non-Patent Documents 1-3).

On the other hand, the present applicant has disclosed utilizing Aureobasidium pullulans, also known as black yeast, which produces β-glucans abundantly, as a moisturizer for skin (Patent Document 1), an agent to improve constipation (Patent Document 2), an immunopotentiator (Patent Document 3), an immunoadjuvant (Patent Document 4), an agent to promote body healing used to reduce the side effects of anticancer drugs (Patent Document 5), an agent to promote body healing used to promote healing of burns (Patent Document 6), a composition for the prevention/treatment of mastitis in cows (Patent Document 7), a composition to promote cytokine production in macrophages (Patent Document 8), an agent for treatment of influenza virus infection (Patent Document 9), a TRAIL expression enhancer (Patent Document 10), a composition for preventing/improving anemia (Patent Document 11), an agent for suppressing fat accumulation (Patent Document 12), etc.

Related Art Documents

Non-Patent Documents

[Non-Patent Document 1] Ishida, Y., Agata, Y., Shibahara, K. and Honjo, T. "Induced expression of PD-1, a novel member of the immunoglobulin gene superfamily, upon programmed cell death." EMBO J. 11 3887-3895 (1992)

[Non-Patent Document 2] Freeman, G. J., Long, A. J., Iwai, Y., Borque, K., Chernova, T., Nishimura, H., Fitsz, L. J., Malenkovich, N., Okazaki, T., Byrne, M. C., Horton, H. F., Fouser, L., Carter, L., Ling, V., Bowman, M. R., Carreno, B. M., Collins, M., Wood, C. R. and Honjo, T. "Engagement of the PD-1 immunoinhibitory receptor by a novel B7 family member leads to negative regulation of lymphocyte activation. J. Exp. Med. 192 1027-1034 (2000)

[Non-Patent Document 3] Spencer C. Wei, Colm R. Duffy, and James P. Allison "Fundamental Mechanisms of Immune Checkpoint Blockade Therapy" CANCER RESEARCH, doi: 10.1158/2159-8290.CD-18-0367, Aug. 16, 2018

Patent Documents

[Patent Document 1] Japanese Patent No. 4000078
[Patent Document 2] Japanese Patent No. 4054697
[Patent Document 3] Japanese Patent No. 4369258
[Patent Document 4] Japanese Patent No. 5242855
[Patent Document 5] Japanese Patent No. 5331482
[Patent Document 6] Japanese Patent No. 5715659
[Patent Document 7] Japanese Patent No. 5554221
[Patent Document 8] Japanese Patent No. 5559173
[Patent Document 9] Japanese Patent No. 5560472
[Patent Document 10] Japanese Patent No. 5937029
[Patent Document 11] Japanese Patent No. 6293187
[Patent Document 12] Japanese Patent No. 6380968

DISCLOSURE OF THE INVENTION

Problems the Invention is Intended to Solve

An object of the present invention is to utilize Aureobasidium pullulans to provide a composition capable of enhancing the effect of an antibody drug such as an immune checkpoint inhibitor, etc.

Means for Solving the Problems

Upon having conducted thoroughgoing studies into achieving the above goal, the present inventors perfected the invention by discovering that the β-glucans contained in cultures of Aureobasidium pullulans act to enhance the effect of antibody drugs such as immune checkpoint inhibitors, etc., when used in combination therewith. Specifically, the present invention is as follows.

[1] A composition for enhancing the effect of an antibody drug characterized by containing a β-glucan as an active ingredient and being administered together with an antibody drug.

[2] The composition for enhancing the effect of an antibody drug according to [1] above, wherein the antibody drug has an effect of suppressing growth of cancer via immune checkpoint inhibition.

[3] The composition for enhancing the effect of an antibody drug according to [1] above, wherein the antibody drug includes a monoclonal antibody to PD-L1.

[4] The composition for enhancing the effect of an antibody drug according to [1] above, wherein the antibody drug has an effect of suppressing growth of melanoma.

Effect of the Invention

In the present invention, a β-glucan is used as an active ingredient; therefore, the effect of the antibody drug can be enhanced by administering together with an antibody drug, allowing suitable use as a potentiator of an immune checkpoint inhibitor, etc.

MODE FOR CARRYING OUT THE INVENTION

In the present invention, a β-glucan is used as an active ingredient of a composition for enhancing the effect of an antibody drug.

β-Glucans are polysaccharides in which β-glucose is polymerized by glycoside bonds. Since β-glucans are contained, for example, in barley, oats, and other such cereals; brewer's yeast, baker's yeast, and other such yeasts; black yeast and other such imperfect fungi; shiitake (Lentinula edodes), maitake (Grifola frondosa), turkey tail mushroom (Coriolus versicolor), split gill mushroom (Schizophyllum commune), cauliflower mushroom (Sparassis crispa), and other such basidiomycetes; and kelp, wakame, and other such seaweeds, β-glucans can be obtained by extraction from these natural materials using a suitable solvent, etc. Usual methods are acceptable as the extraction method and are not particularly restricted. For example, water, hydrous alcohol, or another such extraction solvent is added to a raw material that has been dried and crushed as needed, and extraction is performed under heating and/or pressurization. Heating conditions are typically 105-135° C., and pressurization conditions are typically 1.8-2.1 atm. Extraction may also be carried out while performing acid treatment or alkali treatment or enzyme treatment by an enzyme that lowers the molecular weight of the polysaccharide, to improve the extraction efficiency. After extraction, the solvent may be distilled off to effect concentration, and the product may be dried and converted to a pulverulent form by a drying means such as spray drying. Various β-glucan materials have entered the marketplace in recent years, and such commercial products therefore may be utilized.

The β-glucan used in the present invention is preferably polymerized by β-1,3 glycoside bonds, β-1,4 glycoside bonds, β-1,6 glycoside bonds, etc., more preferably includes homopolymerization of β-1,3 glycoside bonds as the main chain or includes heteropolymerization of β-1,3 glycoside bonds and β-1,6 glycoside bonds as the main chain, and even more preferably includes homopolymerization of β-1,3 glycoside bonds as the main chain and includes β-1,6 glycoside bonds as side chains. β-Glucans may have functional groups such as sulfuric acid groups and phosphoric acid groups. An average molecular weight range of from 5,000 to 1,000,000 is preferred as the molecular weight, and an average molecular weight range of from 200,000 to 500,000 is more preferred. The molecular weight of β-glucans can be measured by gel filtration method, etc.

The β-glucan used in the present invention, as will be shown in the examples below, can be a β-glucan-containing culture composition derived from a culture of *Aureobasidium pullulans* or a β-glucan-containing culture composition derived from shiitake, etc.

β-Glucans derived from microorganisms belonging to *Aureobasidium* sp. will be described in greater detail below. Culture compositions containing such β-glucans include not only cultures obtained by culturing microorganisms belonging to *Aureobasidium pullulans* (sometimes referred to hereinafter as *Aureobasidium* microorganisms), cultures obtained by separating and removing cells by centrifugation, etc., concentrated solutions of said cultures, diluted solutions of said cultures, and solid products obtained by removing the water content from said cultures, but also cultures containing greater amounts of specific components such as β-glucans by desalting or otherwise processing said cultures.

The *Aureobasidium* microorganisms used in the present invention may be any microorganism belonging to *Aureobasidium pullulans* and having the ability to produce β-glucans; e.g., *Aureobasidium pullulans* M-1 (deposit number: FERM BP-08615, deposit date: Feb. 10, 2004, transferred from FERM P-19213 deposited on Feb. 14, 2003) (National Institute of Technology and Evaluation, International Patent Organism Depository, Room 120, 2-5-8 Kazusakamatari, Kisarazu-shi, Chiba-ken, Japan, postal code 292-0818) and *Aureobasidium pullulans* M-2 (deposit number FERM BP-10014, deposit date: Apr. 22, 2004) (National Institute of Technology and Evaluation, International Patent Organism Depository, Room 120, 2-5-8 Kazusakamatari, Kisarazu-shi, Chiba-ken, Japan, postal code 292-0818) is suited for use. Furthermore, structural analysis performed using NMR measurement (13C NMR: model UNITY INOVA 500 manufactured by Varian, 1H NMR: model UNITY INOVA 600 manufactured by Varian) makes clear that the β-glucan produced by these strains is β-1,3-1,6-glucan having a structure in which glucose branches by β-1,6 bonds from a main chain of β-1,3-bonded glucose.

The *Aureobasidium* microorganisms can be cultured in accordance with a known method (see JP (Kokai) Sho 57-149301, etc.). Specifically, medium (pH 5.2-6.0) to which a carbon source (sucrose) 0.5-5.0 mass %, nitrogen source (e.g., rice bran) 0.1-5.0 mass %, and other trace substances (e.g., vitamins, inorganic matter) have been added may be inoculated with fungus and aeration-cultured, preferably aeration-stir-cultured, for 2-14 days at 20-30° C. The viscosity of the culture rises as β-glucan is produced, resulting in a thick, viscous gel. The resulting culture usually includes 0.6-10 mass % of solids, and the solids include 5-80 mass % of β-glucan.

The culture that includes a β-glucan obtained by culturing as described above is preferably sterilized by heating or by pressurization and heating for use. The culture may also be sterilized for use after separating and removing the cells by centrifugation, etc. A culture that has been concentrated or dried as needed can also be used. A culture obtained using an extracted component rich in β-glucans or a desalted, refined product thereof can also be used. Furthermore, cultures of microorganisms belonging to *Aureobasidium*

*pullulans* are used as food additives such as thickening stabilizers and are highly safe.

Due to enhancing the effect of antibody drugs, the composition according to the present invention is administered together with an antibody drug on use. In other words, when the effect of an antibody drug is expressed for the purpose of an anticancer effect, etc., the composition can be used to heighten that effect.

By "administered together with an antibody drug" is meant that both the above β-glucan or β-glucan-containing culture composition and the antibody drug are brought into contact with tissue, cells, or another biological structure that is the target of application in a timely manner within a range that shows their efficacy, it not being necessary that the two are administered in the form of a single formulation. That is, the effect of the present invention can be enjoyed even if the two components are administered continuously, each as separate formulations, or administered at predetermined intervals, within a range that shows their efficacy.

The antibody drug to which the composition according to the present invention is applied is not particularly restricted and can include, for example, an antibody that acts to suppress the growth of a cancer via immune checkpoint inhibition. There are no particular limitations as to the types of diseases and cancers to which antibody drugs can be applied. In the case of cancer, examples include lung cancer, lymphoma, melanoma, leukemia, kidney cell carcinoma, renal pelvis/ureteral cancer, pharyngeal cancer, osteosarcoma, stomach cancer, malignant mesothelioma, ovarian cancer, cervical cancer, pancreatic cancer, MSI-High colon/rectal cancer, esophageal cancer, hepatocellular carcinoma, biliary tract cancer, etc. Anti-PD-L1 antibodies, anti-PD-1 antibodies, anti-LAG3 antibodies, anti-CTLA4 antibodies, anti-TIM3 antibodies, anti-TIGIT antibodies, anti-VISTA antibodies, etc., for example, are known as antibodies, but are not limited to these. The antibody may be a polyclonal antibody, a monoclonal antibody, or in the form of antiserum including an antibody. The antibody may also be an antibody to a human protein or an antibody to a protein of an animal such as a mouse, rat, rabbit, goat, cow, monkey, etc. In addition, the antibody may be a human type antibody or an animal type antibody such as a mouse. Alternatively, the antibody may be prepared by producing an antiserum in an animal such as a mouse, rat, rabbit, goat, cow, monkey, etc.

There is no particular limitation as to the administration route for the composition according to the present invention; known formulation forms can be selected as is appropriate and applied by oral administration, intraperitoneal administration, intramuscular administration, nasal administration, pulmonary administration, vaginal administration, intravenous administration, rectal administration, etc.

The dosage of the composition according to the present invention can be decided as is appropriate depending on the type of antibody drug, health status of the person or animal being administered, symptoms, age, administration method, frequency, time, etc. To give a general example of dosage, in the case of oral intake, the β-glucan or β-glucan-containing culture composition is administered in an amount of 0.025-4000 mg/kg (body weight) in terms of solids. In the case of intraperitoneal administration, the β-glucan or β-glucan-containing culture composition is administered in an amount of 0.05-5 mg/kg (body weight) in terms of solids.

The composition according to the present invention can typically be used in various formulation forms; e.g., as a drug product, topical drug product, functional food, nutritional supplement, supplement, health food, veterinary drug product, veterinary topical drug product, veterinary functional food, veterinary nutritional supplement, veterinary supplement, veterinary health food, etc. Alternatively, these products can be used in combination or in combination with various types of foods and beverages.

EXAMPLES

The present invention is described concretely below through examples, but these examples do not limit the scope of the present invention.

Production Example 1

A β-glucan was produced in culture broth by inoculating liquid medium with *Aureobasidium pullulans* M-2 (National Institute of Technology and Evaluation, International Patent Organism Depository deposit number: FERM BP-10014) and shake culturing for four days at 24.5° C. The β-glucan concentration was estimated to be approximately 6 mg/mL by the phenol-sulfuric acid method and enzyme method.

Test Example 1

Cancer-bearing mice were created by transplantation of a tumor cell line in accordance with the conventional method, and whether administration of the test substance affected growth of the tumors was studied.

Specifically, cancer-bearing mice were created by inoculating the flanks of C57BL/6 mice (Japan SLC) with $3\times10^5$ mouse melanoma cell line B16F10 (Riken BioBank) cells and allowing the tumors to grow for 16 days.

The test animals were divided into four groups: an untreated group, an anti-PD-L1 antibody alone group, a β-glucan alone group, and an anti-PD-L1 antibody and β-glucan combined group. The N number was 26 animals in the untreated group, 18 animals in the anti-PD-L1 antibody alone group, 6 animals in the β-glucan alone group, and 9 animals in the anti-PD-L1 antibody and β-glucan combined group. Below, for the sake of convenience, the untreated group is sometimes referred to as the "control group," the anti-PD-L1 antibody alone group as "test group 1," the β-glucan alone group as "test group 2," and the anti-PD-L1 antibody and β-glucan combined group as "test group 3."

Figure 1:
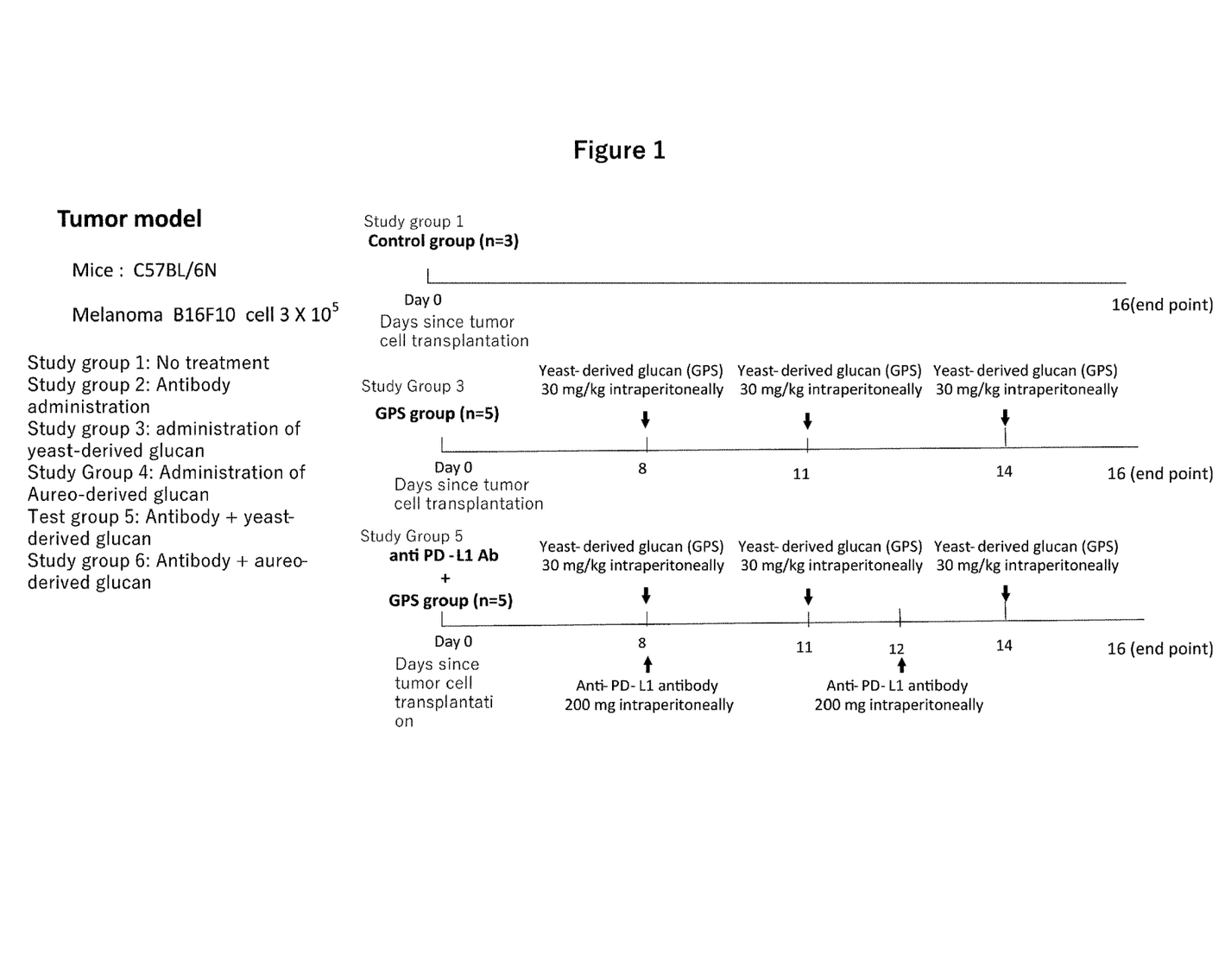
FIG. 1 is a chart showing an outline of the administration schedule of each test substance in Test Example 1.

As the form of the test substance administered, in the anti-PD-L1 antibody alone group ("test group 1"), a dosage of 200 μg/animal of anti-mouse PD-L1 antibody (clone: MIH5) was administered intraperitoneally on days 8 and 12 after tumor cell transplantation. In the β-glucan alone group ("test group 2"), a dosage of 30 mg/kg in terms of β-glucan amount of the β-glucan-containing culture composition prepared in Production example 1 above was administered intraperitoneally on days 8, 11, and 14 after tumor cell transplantation. In the anti-PD-L1 antibody and β-glucan combined group ("test group 3"), anti-mouse PD-L1 antibody and the β-glucan-containing culture composition prepared in Production example 1 above were administered to the mice intraperitoneally in the same dosages as in the respective alone groups at the same times as in the respective alone groups. FIG. 1 shows an overview of the administration schedule of each test substance.

The major and minor axes of the tumors were measured on days 6, 8, 12, 14, and 16 after inoculation of the melanoma cell line, and the tumor volume (in cubic millimeters) determined via the following formula was recorded.

Tumor volume $(mm^3)$ = major axis $(mm) \times (minor\ axis\ (mm))^2 / 2$     Numerical formula 1

Figure 2:
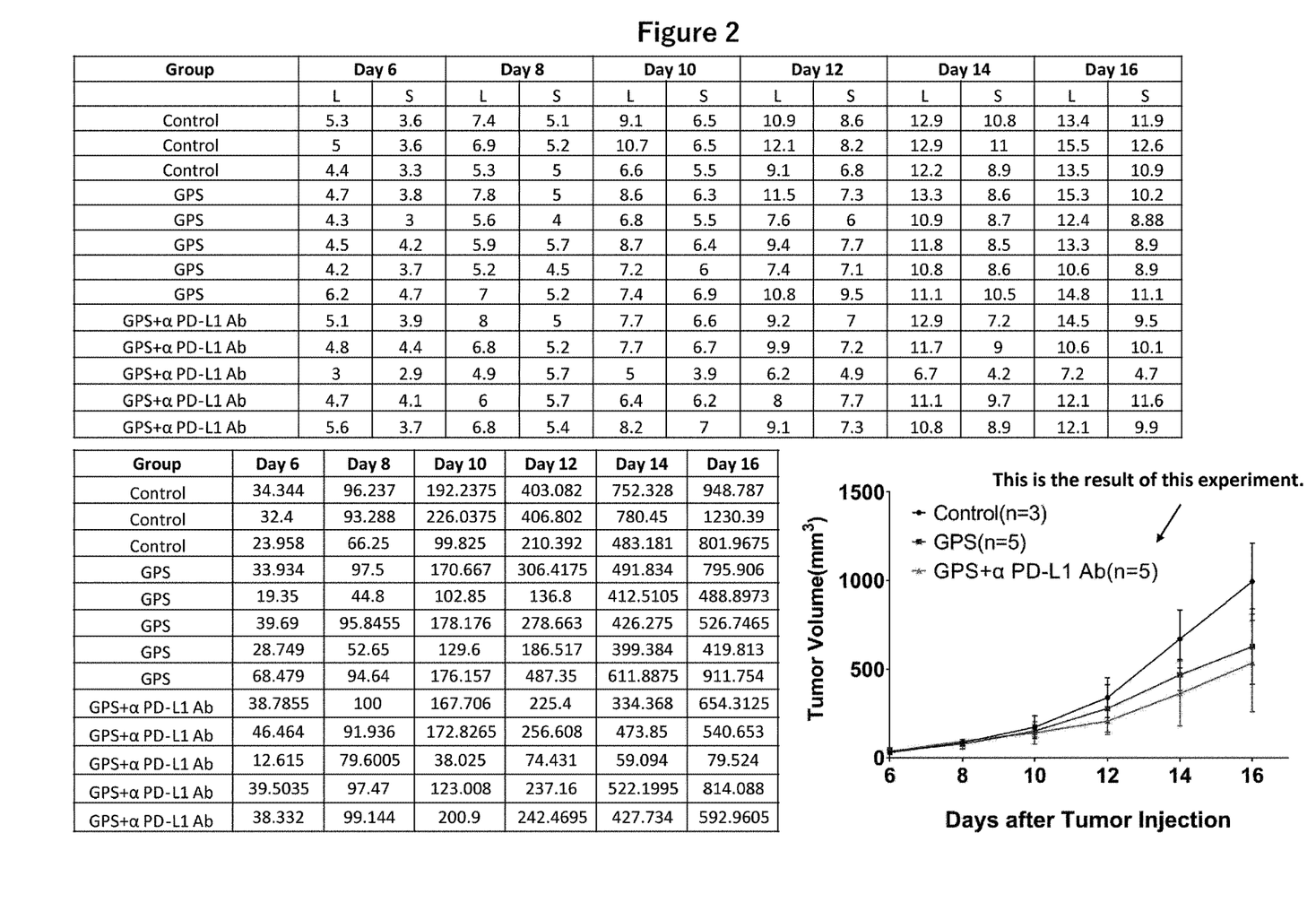
FIG. 2 is a chart showing the results of studying tumor volume after a predetermined number of days from tumor cell transplantation in Test Example 1.

The results on tumor volume after the elapse of the predetermined number of days from tumor cell transplantation are shown in Table 1 and FIG. 2. The results obtained by studying the existence of significance in each group by statistical analysis using the Brown-Forsythe test when comparing tumor volumes on day 16 after tumor cell transplantation are shown in Table 2.

TABLE 1

Tumor volume (mm$^3$) after elapse of number of days from tumor cell transplantation

| | | Day 6 | Day 8 | Day 10 | Day 12 | Day 14 | Day 16 |
|---|---|---|---|---|---|---|---|
| Control group | Mean | 31.28 | 103.36 | 235.27 | 442.66 | 830.32 | 1228.20 |
| | S.D | 15.492 | 48.997 | 75.191 | 154.490 | 333.702 | 372.835 |
| Test group 1 | Mean | 24.78 | 81.86 | 174.60 | 278.79 | 521.86 | 717.79 |
| | S.D | 9.931 | 19.353 | 72.357 | 98.404 | 164.762 | 165.027 |
| Test group 2 | Mean | 16.25 | 69.13 | 102.29 | 197.50 | 415.86 | 681.78 |
| | S.D | 5.671 | 26.833 | 36.520 | 97.133 | 200.289 | 242.078 |
| Test group 3 | Mean | 13.75 | 65.73 | 93.56 | 150.55 | 202.14 | 290.79 |
| | S.D | 4.289 | 27.124 | 44.892 | 75.978 | 54.145 | 73.816 |

TABLE 2

Existence of significance in each group when comparing tumor volumes on day 16 after tumor cell transplantation

| | Significance | Indication | Adjusted p value |
|---|---|---|---|
| Control group vs test group 1 | Yes | **** | <0.0001 |
| Control group vs test group 2 | Yes | *** | 0.0004 |
| Control group vs test group 3 | Yes | **** | <0.0001 |
| Test group 1 vs test group 2 | No | — | 0.9905 |
| Test group 1 vs test group 3 | Yes | ** | 0.003 |
| Test group 2 vs test group 3 | Yes | * | 0.0402 |

In the results, the tumor volume was markedly reduced in the anti-PD-L1 antibody and β-glucan combined group ("test group 3") in comparison to the untreated group ("control group"). The reduction effect was also statistically significant in comparison to the anti-PD-L1 antibody alone group ("test group 1") and the β-glucan alone group ("test group 2") (see comparison on day 16).

Test Example 2

The cancer-bearing mice were necropsied on day 16 after tumor cell transplantation, and spleen lymphocytes and tumor infiltrating lymphocytes (TIL) were separated and purified from cancer-bearing mice of each group. Lymphocytes were prepared using a lymphocyte separation kit (product name "Lympholyte-M", Cedarlane Laboratories) after hemolyzing the collected tissue by sterilized distilled water.

The lymphocytes were stained using anti-mouse CD4 antibody (BioLegend Japan K.K.), anti-mouse CD8 antibody (BioLegend Japan K.K.), anti-mouse Ki-67 (lymphocyte activation marker) antibody (Thermo Fisher Scientific Co., Ltd.), and anti-mouse INF-γ antibody (Becton Dickinson Japan), and FACS analysis was performed. Intracellular antigens were stained after staining the cell surface antigens. Staining of intracellular antigens used Fixation Buffer and Permeabilization Wash Buffer (BioLegend Japan K.K.).

Figure 3:
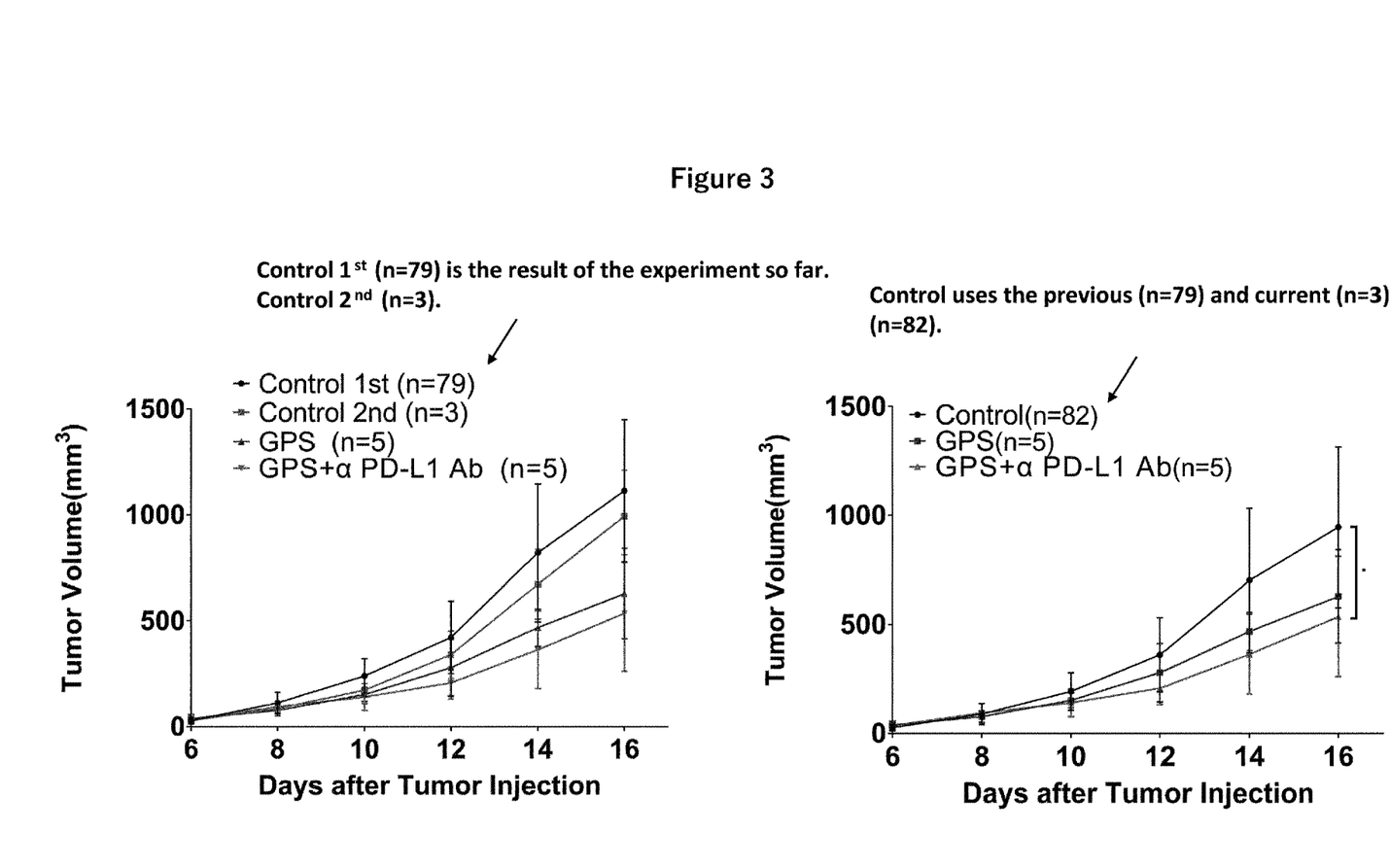
FIG. 3 is a chart showing the results of FACS analysis of spleen lymphocytes after multiple staining by anti-mouse CD4 antibody or instead anti-mouse CD8 antibody and anti-mouse Ki-67 (lymphocyte activation marker) antibody in Test Example 2.

FIG. 3 shows the results of FACS analysis of spleen lymphocytes after multiple staining by anti-mouse CD4 antibody or instead anti-mouse CD8 antibody and anti-mouse Ki-67 (lymphocyte activation marker) antibody.

Figure 4:
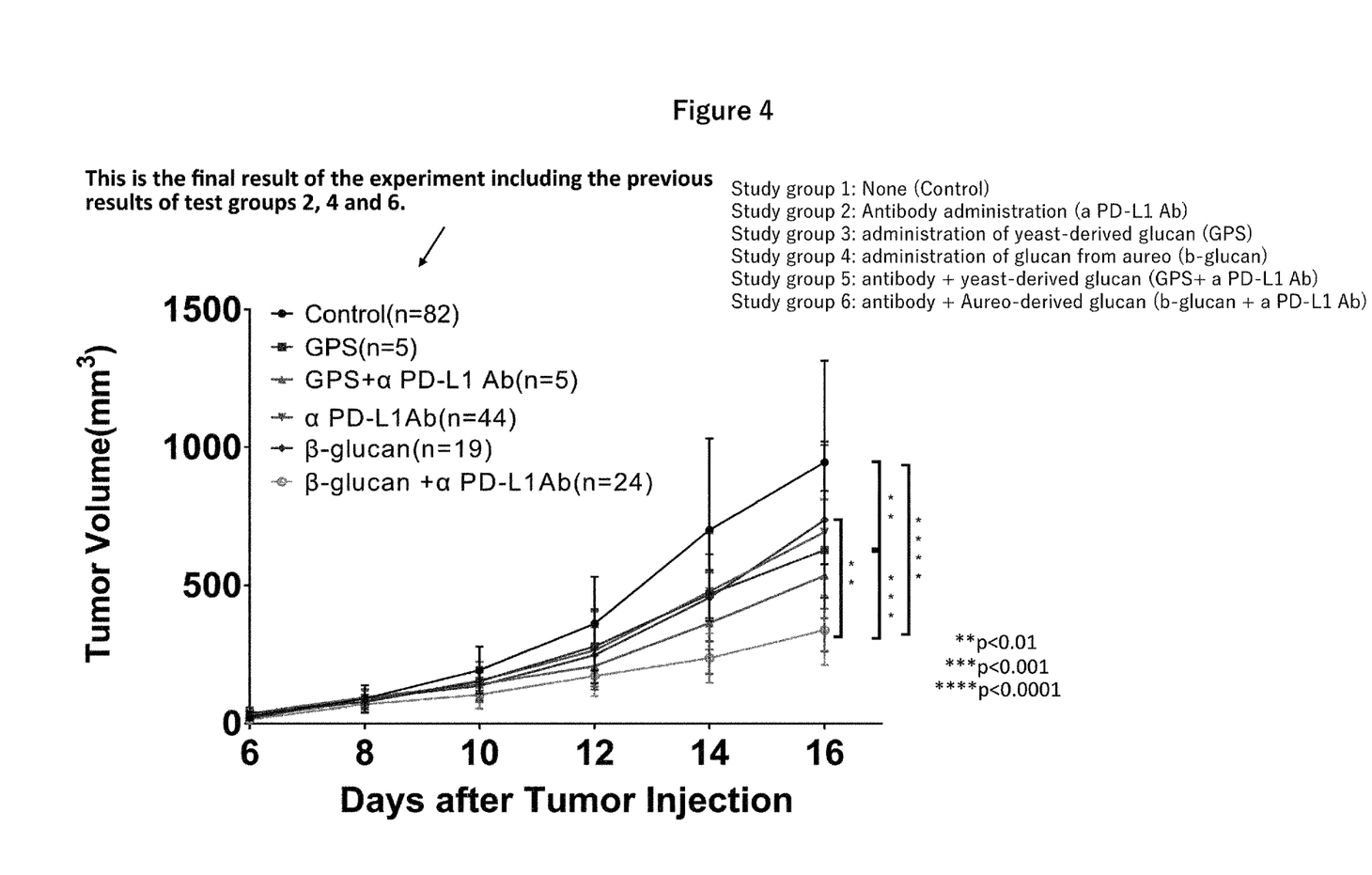
FIG. 4 is a chart showing the results of FACS analysis of tumor infiltrating lymphocytes (TIL) after multiple staining by anti-mouse CD4 antibody or instead anti-mouse CD8 antibody and anti-mouse Ki-67 (lymphocyte activation marker) antibody in Test Example 2.

FIG. 4 shows the results of FACS analysis of tumor infiltrating lymphocytes (TIL) after multiple staining by anti-mouse CD4 antibody or instead anti-mouse CD8 antibody and anti-mouse Ki-67 (lymphocyte activation marker) antibody.

Figure 5:
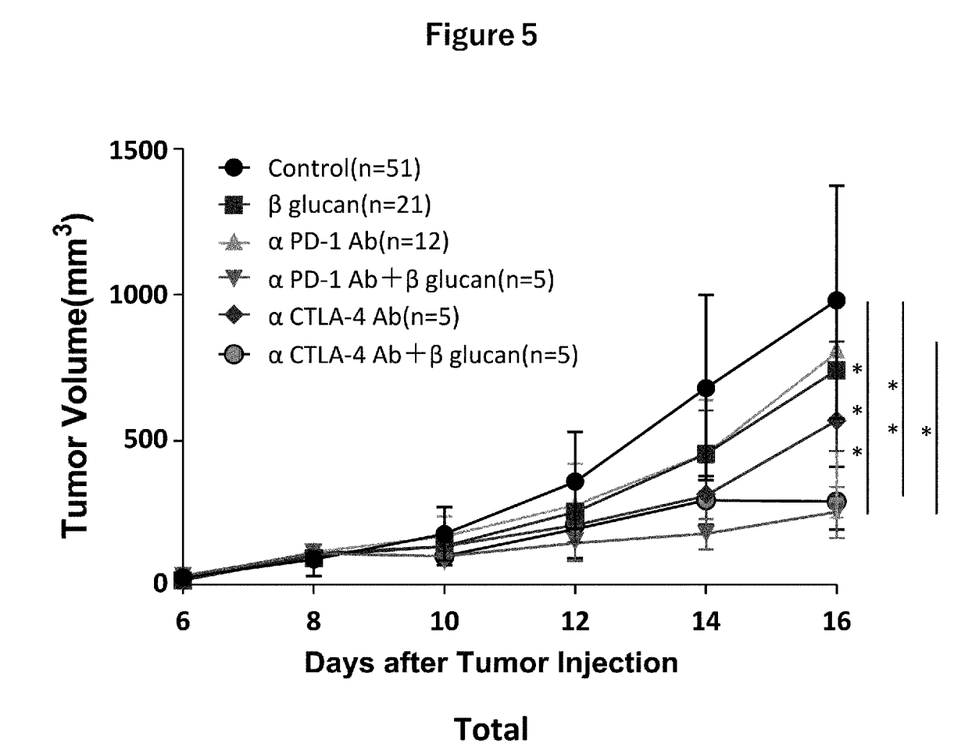
FIG. 5 is a chart showing the results of FACS analysis of spleen lymphocytes after multiple staining by anti-mouse CD4 antibody or instead anti-mouse CD8 antibody and anti-mouse INF-γ antibody in Test Example 2.

FIG. 5 shows the results of FACS analysis of spleen lymphocytes after multiple staining by anti-mouse CD4 antibody or instead anti-mouse CD8 antibody and anti-mouse INF-γ antibody.

Figure 6:
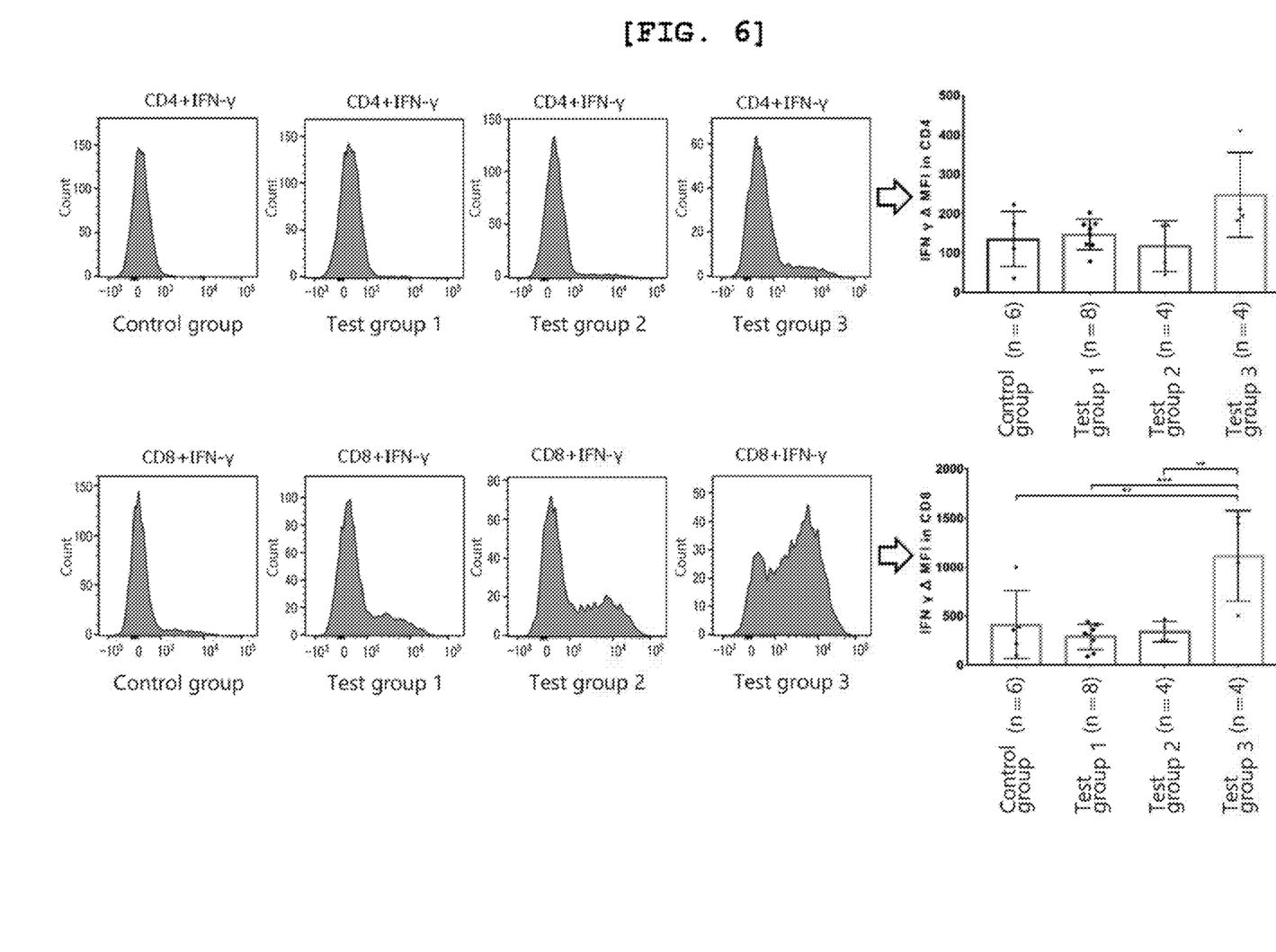
FIG. 6 is a chart showing the results of FACS analysis of tumor infiltrating lymphocytes after multiple staining by anti-mouse CD4 antibody or instead anti-mouse CD8 antibody and anti-mouse INF-γ antibody in Test Example 2.

FIG. 6 shows the results of FACS analysis of tumor infiltrating lymphocytes (TIL) after multiple staining by anti-mouse CD4 antibody or instead anti-mouse CD8 antibody and anti-mouse INF-γ antibody.

As seen in the results in FIG. 3, as regards Ki-67 expression of spleen lymphocytes, no conspicuous differences from the untreated group ("control group") could be found in the anti-PD-L1 antibody alone group ("test group 1") or the β-glucan alone group ("test group 2") or the anti-PD-L1 antibody and β-glucan combined group ("test group 3") in both CD4+ T cells and CD8+ T cells.

As seen in the results in FIG. 4, as regards Ki-67 expression of tumor infiltrating lymphocytes, expression tended to be markedly higher in the anti-PD-L1 antibody and β-glucan combined group ("test group 3") in comparison to the untreated group ("control group") or the anti-PD-L1 antibody alone group ("test group 1") or the β-glucan alone group ("test group 2") in both CD4+ T cells and CD8+ T cells (in FIG. 4, "" indicates $p<0.01$, "*" indicates $<0.001$).

As seen in the results in FIG. 5, as regards INF-γ expression of spleen lymphocytes, no conspicuous differences from the untreated group ("control group") could be found in the anti-PD-L1 antibody alone group ("test group 1") or the β-glucan alone group ("test group 2") or the anti-PD-L1 antibody and β-glucan combined group ("test group 3") in both CD4+ T cells and CD8+ T cells.

As seen in the results in FIG. 6, as regards INF-γ expression of tumor infiltrating lymphocytes, expression tended to be markedly higher in the anti-PD-L1 antibody and β-glucan combined group ("test group 3") in comparison to the untreated group ("control group") or the anti-PD-L1 antibody alone group ("test group 1") or the β-glucan alone group ("test group 2") in CD8+ T cells. On the other hand, in CD4+ T cells, virtually no difference could be seen between the untreated group ("control group") and the anti-PD-L1 antibody and β-glucan combined group ("test group 3") (in FIG. 6, "" indicates p<0.01, "*" indicates p<0.001).

Based on the above, it was clear that administration of anti-PD-L1 antibody and β-glucan activated cell infiltrating T cells and heightened the cytotoxicity thereof. On the other hand, there were no marked effects in spleen lymphocytes. It was also clear that the activating effect was markedly heightened by combined use over administration alone. These results agree well with the tumor volume reduction effect in cancer-bearing mice.

Test Example 3

Cancer-bearing mice were created by transplantation of a tumor cell line in the same way as in Test example 1, and whether administration of the test substance had an effect on growth of the tumors was studied. In this instance, a β-glucan derived from shiitake ("Micelle Glucan," manufactured by RL-JP Co., Ltd.) (referred to hereinafter as "Micelle β-glucan" hereinafter) was used instead of the β-glucan derived from *Aureobasidium pullulans* as the test substance.

Specifically, cancer-bearing mice were created by inoculating the flanks of C57BL/6 mice (Japan SLC) with $3 \times 10^5$ mouse melanoma cell line B16F10 (Riken Biobank) cells and allowing the tumors to grow for 13 days.

The test animals were divided into four groups: an untreated group, a Micelle β-glucan alone group, an anti-PD-L1 antibody alone group, and an anti-PD-L1 antibody and Micelle β-glucan combined group. The N number was 4 animals in the untreated group, 2 animals in the Micelle β-glucan alone group, 3 animals in the anti-PD-L1 antibody alone group, and 3 animals in the anti-PD-L1 antibody and Micelle β-glucan combined group. Below, for the sake of convenience, the untreated group is sometimes referred to as "control group A," the Micelle β-glucan alone group as "test group 1A," the anti-PD-L1 antibody alone group as "test group 2A," and the anti-PD-L1 antibody and Micelle β-glucan combined group as "test group 3A."

Figure 7:
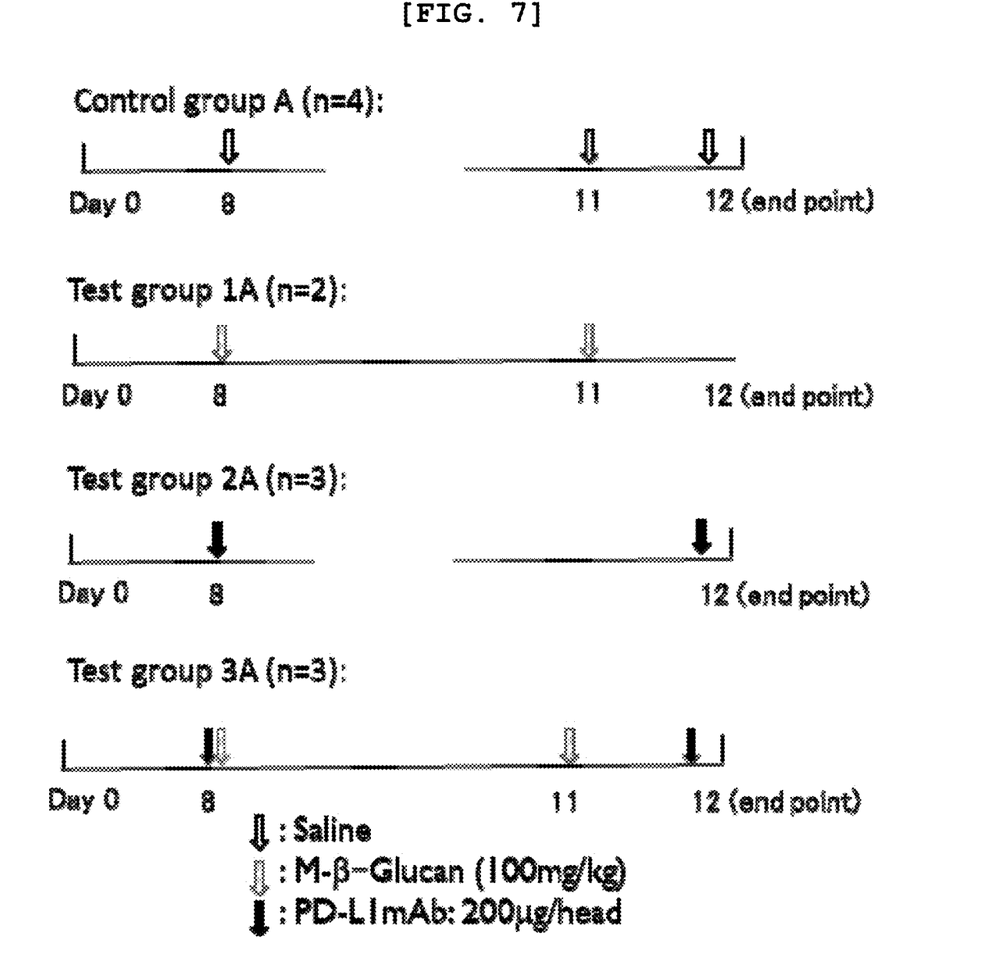
FIG. 7 is a showing an outline of the administration schedule of each test substance in Test Example 3.

As the form of the test substance administered, in the untreated group ("control group A"), physiological saline was administered intraperitoneally on days 8, 12, and 14 after tumor cell transplantation. In the Micelle β-glucan alone group ("test group 1A"), Micelle β-glucan was administered intraperitoneally in a dosage of 100 mg/kg in terms of the β-glucan amount on days 8 and 11 after tumor cell transplantation. In the anti-PD-L1 antibody alone group ("test group 2A"), anti-mouse PD-L1 antibody (clone: MIH5) was administered intraperitoneally in a dosage of 200 μg/animal on days 8 and 12 after tumor cell transplantation. In the anti-PD-L1 antibody and Micelle β-glucan combined group ("test group 3A"), anti-mouse PD-L1 antibody was administered in the same dosage form as above on days 8 and 12 after tumor cell transplantation and Micelle β-glucan was administered intraperitoneally in a dosage of 100 mg/kg in terms of the β-glucan on days 8 and 11 after tumor cell transplantation. FIG. 7 shows an overview of the administration schedule of each test substance.

The major and minor axes of the tumors were measured on days 6, 8, 11, and 12 after inoculation of the melanoma cell line, and the tumor volume ($mm^3$) was recorded in the same way as in Test example 1.

Figure 8:
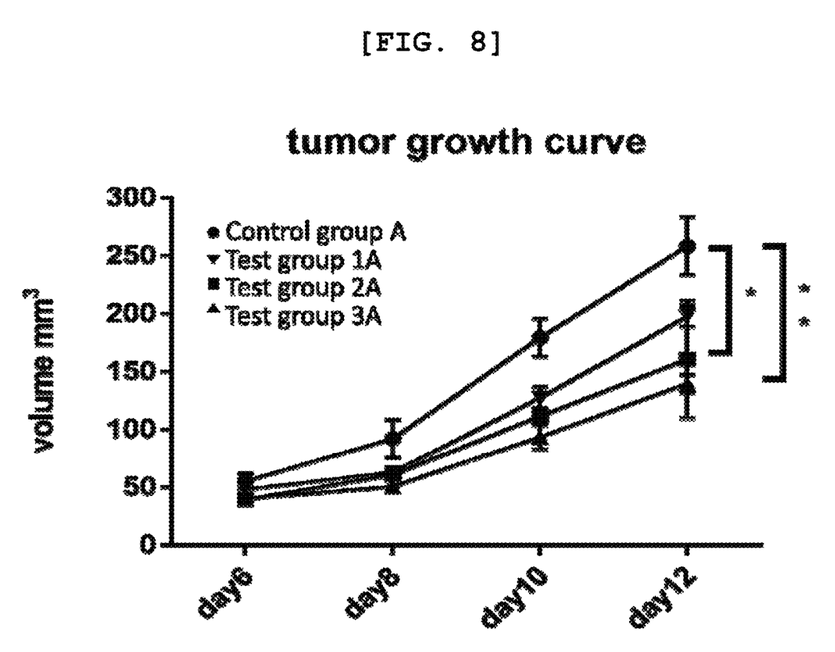
FIG. 8 is a chart showing the results of studying tumor volume after a predetermined number of days from tumor cell transplantation in Test Example 3.

The results on tumor volume after the elapse of the predetermined number of days from tumor cell transplantation are shown in Table 3 an FIG. 8. The results obtained by studying the existence of significance in each group by statistical analysis by the Brown-Forsythe test when comparing tumor volumes on day 12 after tumor cell transplantation are shown in Table 4.

TABLE 3

| | Tumor volume ($mm^3$) after elapse of number of days from tumor cell transplantation | | | |
|---|---|---|---|---|
| | Day 6 | Day 8 | Day 10 | Day 12 |
| Control group A | 45.50 | 71.66 | 176.16 | 221.78 |
| | 62.96 | 94.22 | 196.99 | 278.40 |
| | 55.23 | 90.75 | 158.44 | 267.70 |
| | 59.25 | 111.60 | 185.68 | 265.24 |
| Test group 1A | 43.22 | 63.75 | 120.93 | 191.56 |
| | 53.24 | 61.85 | 134.54 | 204.16 |
| Test group 2A | 34.22 | 56.07 | 113.40 | 136.46 |
| | 39.75 | 64.51 | 104.28 | 126.85 |
| | 44.38 | 61.06 | 117.21 | 219.38 |
| Test group 3A | 41.60 | 50.78 | 104.28 | 140.31 |
| | 40.57 | 45.50 | 92.70 | 147.46 |
| | 37.93 | 55.30 | 83.82 | 132.10 |

TABLE 4

Existence of significance in each group when comparing tumor volumes on day 12 after tumor cell transplantation

| | Significance | Indication | Adjusted P value |
|---|---|---|---|
| Control group A vs test group 2A | Yes | * | 0.0128 |
| Control group A vs test group 3A | Yes | ** | 0.0046 |
| Test group 2A vs test group 3A | No | — | 0.7141 |

In the results, the tumor volume was markedly lower in the anti-PD-L1 antibody and Micelle β-glucan combined group ("test group 3A") in comparison to the untreated group ("control group A"). The reduction effect tended to be higher than in the anti-PD-L1 antibody alone group ("test group 2A") (see comparison on day 12).

The invention claimed is:

1. A method for enhancing the effect of an antibody drug, the method comprising:
   administrating a composition containing a β-glucan as an active ingredient together with the antibody drug to a melanoma patient in need thereof,
   wherein the β-glucan is derived from *Aureobasidium pullulans;*
   wherein the antibody drug suppresses growth of melanoma via immune checkpoint inhibition, wherein said administering provides a synergistic suppressive effect on the growth of melanoma, and the antibody drug is a monoclonal antibody to PD-L1.

* * * * *